United States Patent [19]

Yamazaki et al.

[11] Patent Number: 5,756,437
[45] Date of Patent: May 26, 1998

[54] AQUEOUS GEL CLEANSER COMPRISING FATTY ACID ESTER OF PEG AS NONIONIC SURFACTANT

[75] Inventors: Ritsuko Yamazaki; Reiko Fukuda; Yasushi Kajihara, all of Tokyo, Japan

[73] Assignee: Kao Corporation, Tokyo, Japan

[21] Appl. No.: 630,898

[22] Filed: Apr. 4, 1996

[30] Foreign Application Priority Data

Apr. 10, 1995 [JP] Japan ................. 7-083718

[51] Int. Cl.$^6$ .............. C11D 17/00; C11D 3/22; C11D 3/37; A61K 7/02
[52] U.S. Cl. ............ 510/136; 510/137; 510/158; 510/403; 510/421; 510/422; 510/434; 510/470; 510/471; 510/473; 510/474; 510/506
[58] Field of Search ............ 510/158, 136–138, 510/159, 403, 421, 434, 437, 470, 471, 473, 474, 491, 505, 506, 422

[56] References Cited

U.S. PATENT DOCUMENTS

| | | | |
|---|---|---|---|
| 3,277,013 | 10/1966 | Gianladis | 252/153 |
| 4,097,403 | 6/1978 | Tsutsumi et al. | 252/312 |
| 5,011,681 | 4/1991 | Ciotti et al. | 424/81 |
| 5,462,691 | 10/1995 | Shimada et al. | 510/158 |
| 5,474,776 | 12/1995 | Koyanagi et al. | 424/401 |

FOREIGN PATENT DOCUMENTS

| | | |
|---|---|---|
| 62-26213 | 2/1987 | Japan . |
| 4-120012 | 4/1992 | Japan . |
| 7-215840 | 8/1995 | Japan . |
| 7-215842 | 8/1995 | Japan . |
| 7-216386 | 8/1995 | Japan . |

OTHER PUBLICATIONS

English translation of JP 7–215840, published Aug. 15, 1995, May 1997.
English translation of JP 7–216386, published Aug. 15, 1995, May 1997.
English translation of JP 62-26213, published Feb. 4, 1987, May 1997.
English translation of JP 4-120012, published Apr. 21, 1992, May 1997.

*Primary Examiner*—Ardith Hertzog
*Attorney, Agent, or Firm*—Oblon, Spivak, McClelland, Maier & Neustadt, P.C.

[57] ABSTRACT

An aqueous gel cleanser composition which contains:

(A) from 1 to 50% by weight of a nonionic surfactant represented by the formula (1):

$$RCOO-(CH_2CH_2O)_n-H \qquad (1)$$

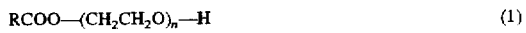

wherein RCO represents a saturated or unsaturated acyl group having 4 to 30 carbon atoms; and n represents a number of from 1 to 50 on the weight average;

(B) from 20 to 70% by weight of a polyhydric alcohol or a glycol ether; and (C) from 0.1 to 5% by weight of a water soluble polymer.

This aqueous gel cleanser composition has a high detergency on makeup stains and sebum stains, little irritates the skin, exhibits a good massaging effect and is usable even at high temperatures and humidity owing to its high stability.

7 Claims, No Drawings

AQUEOUS GEL CLEANSER COMPRISING FATTY ACID ESTER OF PEG AS NONIONIC SURFACTANT

FIELD OF THE INVENTION

This invention relates to an aqueous gel cleanser composition which has a high detergency on makeup stains and sebum stains, little irritates the skin, exhibits a good massaging effect and good rinsing properties and is usable even at high temperatures and humidity owing to its high stability.

BACKGROUND OF THE INVENTION

Makeup products (lipstick, foundation, eye shadow, mascara, etc.), which are rich in oily components and solid fats, can be only insufficiently solubilized or emulsified by using the conventional solid or pasty facial cleansers containing soaps as the main component. Accordingly, makeup stains can be hardly removed by using these cleansers. To remove these makeup stains, there have been employed gel cleansers, cleansing creams, cleansing oils, etc. comprising oily bases as the main component.

However, sebum stains including solid stains filling up pores can be only insufficiently removed with these cleansers comprising oily bases as the main component. Moreover, these products impart an oily feel after using. It is therefore needed to wash the face again with a pasty facial cleanser, etc. after using such a cleanser. When used at high temperatures and humidity, the stability of a cleanser comprising oily bases as the main component is worsened due to the moisture contained therein. As a result, there arise some problems of separation and deterioration in detergency. Furthermore, a cleanser having a low viscosity (for example, cleansing oil) has another disadvantage of running down from the face and thus soiling clothes during cleansing.

It is also required that a cleanser composition for removing oily stains (makeup stains, sebum stains, etc.) is little irritative to the skin. However, products comprising common fatty acid soaps or anionic surfactants as a base are highly irritative to the skin in general. Although a product comprising a nonionic surfactant as a base has a low irritativeness and a high detergency, the detergency of the surfactant is considerably deteriorated when the product is thickened in order to facilitate massaging.

Accordingly, an object of the present invention is to provide an aqueous gel cleanser composition which has a high detergency on makeup stains and sebum stains, little irritates the skin, exhibits a good massaging effect and is usable even at high temperatures and humidity owing to its high stability.

SUMMARY OF THE INVENTION

Under these circumstances, the present inventors have conducted extensive studies. As a result, they have successfully found out that an aqueous gel cleanser composition, which has a high detergency on oily stains (makeup stains, sebum stains, etc.), little irritates the skin, is easily applicable to the face or hand, exhibits a good massaging effect and good rinsing properties, and is usable even at high temperatures and humidity owing to its high stability, can be obtained by combining a specific nonionic surfactant, a polyhydric alcohol or a glycol ether and a water soluble polymer at a specific ratio, thus completing the present invention.

Accordingly, the present invention provides an aqueous gel cleanser composition containing the following components (A), (B) and (C):

(A) from 1 to 50% by weight of a nonionic surfactant represented by the formula (1):

$$RCOO-(CH_2CH_2O)_n-H \qquad (1)$$

wherein RCO represents a saturated or unsaturated acyl group having 4 to 30 carbon atoms; and n represents a number of from 1 to 50 on the weight average;

(B) from 20 to 70% by weight of a polyhydric alcohol or a glycol ether; and (C) from 0.1 to 5% by weight of a water soluble polymer.

DETAILED DESCRIPTION OF THE INVENTION

The nonionic surfactant to be used as the component (A) in the present invention is a higher fatty acid ester of polyethylene glycol represented by the above formula (1). In this formula, RCO represents a saturated or unsaturated acyl group having 4 to 30 carbon atoms, preferably those having 10 to 22 carbon atoms (for example, caprinoyl, lauroyl, myristoyl, palmitoyl, stearoyl, etc.), and n represents a number of from 1 to 50 on the weight average. It is preferable that n is a number of from 10 to 30, since an enhanced power of solubilizing makeup stains can be thus obtained.

Compared with the corresponding ether type nonionic surfactants, these ester type nonionic surfactants represented by the formula (1) have less potent cytotoxicity, less irritativeness to the skin and higher detergency on oily stains.

Either one of these nonionic surfactants or a combination thereof may be used as the component (A). The content of the component (A) in the total composition ranges from 1 to 50% by weight, preferably from 5 to 30% by weight and still preferably from 10 to 20% by weight. When the content thereof falls within this range, the composition shows a sufficient detergency, no tackiness when applied to the skin, gives a good massaging effect and can be easily rinsed off with water.

The component (B) employed in the present invention is a polyhydric alcohol or a glycol ether. Examples of the polyhydric alcohol include ethylene glycol, propylene glycol, isoprene glycol, dipropylene glycol, 1,3-butylene glycol, diethylene glycol, dipropylene glycol, glycerol, pentaerythritol and sorbitol. Examples of the glycol ether include ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol monobutyl ether, propylene glycol monomethyl ether, propylene glycol monoethyl ether and ethylene glycol monophenyl ether.

Among these materials, it is particularly preferable to use ethylene glycol, propylene glycol, isoprene glycol, dipropylene glycol, glycerol, 1,3-butylene glycol, sorbitol or diethylene glycol monoethyl ether therefor.

Either one of these polyhydric alcohols or glycol ethers or a combination thereof may be used as the component (B). It is particularly preferable to use a combination of two or more of the same. The content of the component (B) in the total composition ranges from 20 to 70% by weight, preferably from 20 to 50% by weight and still preferably from 20 to 40% by weight. When the content thereof falls within this range, the composition shows a sufficient detergency and remains stable without showing any separation.

As the water soluble polymer to be used as the component (C) in the present invention, either a natural polymer or a synthetic one may be used, so long as it is soluble in water. Examples thereof include pectin, carrageenan, guar gum, locust bean gum, gelatin, xanthan gum, carboxyvinyl polymer, carboxymethylhydroxyethylcellulose, hydroxyethylcellulose, alginates, starch, polyvinyl alcohol, polyacrylates, polymethylacrylates and polyethylene glycol. Among these materials, it is particularly preferable to use carrageenan, carboxyvinyl polymer and hydroxyethylcellulose. Among all, the most desirable one is κ-carrageenan optionally combined with another water soluble polymer such as xanthan gum or ι-carrageenan.

Either one of these water soluble polymers or a combination thereof may be used as the component (C). The content of the component (C) in the total composition ranges from 0.1 to 5% by weight, preferably from 0.1 to 3% by weight and still preferably from 0.3 to 1% by weight. When the content thereof falls within this range, a good massaging effect and a sufficient detergency can be obtained at using.

The aqueous gel cleanser composition of the present invention may further contain a nonionic surfactant other than the component (A) to thereby improve the detergency and the stability. Examples of such a nonionic surfactant include polyoxyethylene sorbitan fatty acid esters, ethylene oxide derivatives of glycerol fatty acid esters, ethylene oxide derivatives of propylene glycol fatty acid esters, polyoxyethylene alkyl ethers, polyoxypropylene alkyl ethers, polyoxyethylene alkylphenyl ethers and polyoxyethylene hardened castor oil. It is preferable to use therefor those having HLB of at least 10, still preferably at least 12. It is preferable to control the weight ratio of such an additional nonionic surfactant to the nonionic surfactant of the component (A) to 1/10 to 10/1, still preferably 1/4 to 4/1 and still preferably 1/2 to 2/1, since the detergency and rinsing properties can be further improved thereby.

The aqueous gel cleanser composition of the present invention may contain various oily components in an amount up to about 5% by weight. In addition to the above-mentioned components, it may optionally contain various components commonly employed in cleanser compositions (for example, humectants, bactericides, preservatives, chelating agents, electrolytes, medicinal components, coloring matters, perfumes, antioxidants, pH regulators), so long as the effects of the present invention are not deteriorated thereby.

The aqueous gel cleanser composition of the present invention is produced by mixing the above-mentioned components with water at such a composition ratio as to give a gel product. The desired viscosity can be obtained by controlling the content of each component. It is preferable to establish a viscosity capable of giving good handling properties, etc., for example, from 10,000 to 60,000 cps when measured with a Brookfield type viscometer.

The aqueous gel cleanser composition thus obtained is usable in cleansing, etc. It is particularly suitable as a facial cleanser for removing makeup products, etc.

Although the aqueous gel cleanser composition of the present invention little irritates the skin, it has a good detergency on oily stains (makeup stains, sebum stains, etc.) and good rinsing properties. Moreover, it is excellent in shape retention and easily applicable to the face or hand and exhibits a good massaging effect. Because of having a high stability, furthermore, it is usable even at high temperatures and humidity without any deterioration in the performance.

To further illustrate the present invention in greater detail, and not by way of limitation, the following Examples will be given.

EXAMPLE 1

Aqueous gel cleanser compositions as specified in Tables 1 and 2 were produced by the following method and evaluated in appearance, detergency, massaging effect, rinsing properties, stability and skin irritation. The results are given in Tables 1 and 2. A dispersion of the water soluble polymer in the polyhydric alcohol and the glycol ether was slowly added to water under heating. Next, the nonionic surfactant was added thereto and the resulting mixture was thoroughly stirred and then cooled.

(Evaluation Method)

(1) Appearance

Immediately after the production, the appearance of each product was evaluated with the naked eye on the basis of the following criteria.

⊚: very good.

○: good.

Δ: moderate.

×: poor.

(2) Detergency

A lipstick was applied in a definite amount to the inside of the lower arm of a subject. Then the applied part was massaged with the use of each cleanser composition under a definite pressure in a definite number followed by washing off. Then the color difference was measured and thus the detergency was determined in percentage. The detergency was evaluated in accordance with the following criteria.

⊚: ≧80%.

○: 70–80%.

Δ: 50–70%.

×: <50%.

(3) Massaging Effect

Each cleanser composition was applied to the face of a skilled panelist. After massaging under a definite pressure in a definite number, the smoothness and the texture were evaluated in accordance with the following criteria.

○: highly stretchable.

Δ: moderate.

×: less stretchable.

(4) Rinsing Properties

Each cleanser composition was applied to the face of a skilled panelist. After massaging for 20 seconds, it was rinsed off with a definite amount of water. Based on the residue, the rinsing properties were evaluated in accordance with the following criteria.

⊚: quickly rinsed off.

Δ: moderate.

×: scarcely rinsed off.

(5) Stability

Each cleanser composition was stored in a thermostat at 40° C. After 3 months, the appearance was evaluated in accordance with the following criteria.

⊚: very good.

○: good.

Δ: cloudiness, change in viscosity.

×: separated.

(6) Irritativeness to Eye

By using culture cells originating in rabbit cornea, the concentration at which the growth of the cells was inhibited at a ratio of 50% ($IC_{50}$) was calculated. The irritativeness was evaluated in accordance with the following criteria.

Low irritativeness: $IC_{50} \geqq 500$ ppm.

Moderate irritativeness: 200 ppm $\leqq IC_{50} < 500$ ppm.

High irritativeness: $IC_{50} < 200$ ppm.

TABLE 1

| Component (wt. %) | Invention product | | | | | | | | |
|---|---|---|---|---|---|---|---|---|---|
| | 1 | 2 | 3 | 4 | 5 | 6 | 7 | 8 | 9 |
| polyethylene glycol monolaurate (n = 12) | 30 | | | 20 | 20 | 20 | 20 | 14 | 14 |
| polyethylene glycol monolaurate (n = 20) | | 30 | | | | | | | |
| polyethylene glycol monoisostearate (n = 12) | | | 30 | | | | | | |
| polyoxyethylene (12) lauryl ether | | | | | | | | | |
| polyoxyethylene (20) octyl dodecyl ether | | | | | | | | | |
| polyoxyethylene (6) sorbitan coconut oil fatty acid ester | | | | 10 | | | | 4 | 4 |
| polyoxyethylene (20) sorbitan monoisostearate | | | | | | 10 | 10 | 10 | 12 | 12 |
| glycerol | | | | | 20 | | | | 20 |
| diethylene glycol monoethyl ether | 20 | 20 | 20 | 20 | 20 | 20 | 20 | 15 | 15 |
| sorbitol | 20 | 20 | 20 | 20 | | 20 | 20 | 20 | |
| l-carrageenan | 0.2 | 0.2 | 0.2 | 0.2 | 0.2 | | | 0.2 | 0.2 |
| κ-carrageenan | 0.3 | 0.3 | 0.3 | 0.3 | 0.3 | | | 0.3 | 0.3 |
| carboxyvinyl polymer | | | | | | 0.5 | | | |
| hydroxyethylcellulose | | | | | | | 0.5 | | |
| polyisobutene | | | | | | | | | |
| water | 29.5 | 29.5 | 29.5 | 29.5 | 29.5 | 29.5 | 29.5 | 34.5 | 34.5 |
| appearance | ○ | ○ | ○ | ◎ | ○ | ○ | ○ | ◎ | ◎ |
| detergency | ○ | ○ | ○ | ◎ | ○ | ○ | ○ | ○ | ○ |
| massaging effect | ○ | ○ | ○ | ○ | ○ | ○ | ○ | ○ | ○ |
| rinsing properties | ○ | ○ | ○ | ○ | ○ | ○ | ○ | ○ | ○ |
| stability | ◎ | ◎ | ◎ | ◎ | ○ | ○ | ○ | ◎ | ◎ |
| skin irritation | low | low | low | low | low | low | low | low | low |

TABLE 2

| Component (wt. %) | Invention | | Comparison | | | | | | |
|---|---|---|---|---|---|---|---|---|---|
| | 10 | 11 | 1 | 2 | 3 | 4 | 5 | 6 | 7 |
| polyethylene glycol monolaurate (n = 12) | 14 | 14 | | | | | | 30 | 30 |
| polyethylene glycol monolaurate (n = 20) | | | | | | | | | |
| polyethylene glycol monoisostearate (n = 12) | | | | | | | | | |
| polyoxyethylene (12) lauryl ether | | | 30 | | | | | | |
| polyoxyethylene (20) octyl dodecyl ether | | | | 30 | | | | | |
| polyoxyethylene (6) sorbitan coconut oil fatty acid ester | 4 | 4 | | | 30 | | 15 | | |
| polyoxyethylene (20) sorbitan monoisostearate | 12 | 12 | | | | 30 | 15 | | |
| glycerol | | | | | | | | | |
| diethylene glycol monoethyl ether | 15 | 15 | 20 | 20 | 20 | 20 | 20 | | 20 |
| sorbitol | 20 | 20 | 20 | 20 | 20 | 20 | 20 | | 20 |
| l-carrageenan | 0.1 | | 0.2 | 0.2 | 0.2 | 0.2 | 0.2 | 0.2 | 0.2 |
| κ-carrageenan | | 0.1 | 0.3 | 0.3 | 0.3 | 0.3 | 0.3 | 0.3 | 0.3 |
| carboxyvinyl polymer | 0.4 | 0.4 | | | | | | | |
| hydroxyethylcellulose | | | | | | | 0.5 | | |
| polyisobutene | | | | | | | | | |
| water | 34.5 | 34.5 | 29.5 | 29.5 | 29.5 | 29.5 | 29.5 | 69.5 | 30 |
| appearance | ◎ | ◎ | ○ | Δ | ○ | ○ | ○ | Δ | x |
| detergency | ◎ | ◎ | Δ | x | Δ | x | x | Δ | ○ |
| massaging effect | ○ | ○ | ○ | x | ○ | ○ | ○ | ○ | x |
| rinsing properties | ○ | ○ | x | x | x | x | x | Δ | ○ |
| stability | ◎ | ◎ | x | x | x | x | ○ | x | x |
| skin irritation | low | low | high | high | low | low | low | low | low |

EXAMPLE 2

An aqueous gel cleanser composition of the following composition was produced by a conventional method.

The cleanser composition thus obtained had a good detergency on oily stains, little irritated the skin, showed a good performance (massaging effect, etc.) and could be used even at high temperatures and humidity owing to the high stability.

| (Component) | (% by weight) |
|---|---|
| polyethylene glycol monolaurate (n = 12) | 14.0 |
| polyoxyethylene (20) sorbitan isostearate | 12.0 |
| diethylene glycol ethyl ether | 15.0 |
| sorbitol solution (70%) | 20.0 |
| l-carrageenan | 0.2 |
| κ-carrageenan | 0.4 |
| dibutylhydroxytoluene | 0.1 |

| (Component) | (% by weight) |
| --- | --- |
| perfume | 0.1 |
| purified water | the balance |
| | 100.0. |

EXAMPLE 3

20% by weight of a sorbitol solution (70%) was added to water. 0.2% by weight of xanthan gum and 0.4% by weight of κ-carrageenan were dispersed in 15% by weight of diethylene glycol ethyl ether and slowly added to water under heating. Further, 14% by weight of POE (12) monolaurate, 12% by weight of POE (20) sorbitan isostearate and 2% by weight of POE (6) sorbitan coconut fatty acid ester were added thereto. After thoroughly stirring, the mixture was cooled to thereby give the target transparent gel.

The cleanser composition thus obtained had a good detergency on oily stains, little irritated the skin, showed excellent performance (massaging effect, etc.) and could be used even at high temperatures and humidity owing to the high stability.

| (Component) | (% by weight) |
| --- | --- |
| polyethylene glycol monolaurate (n = 12) | 14.0 |
| polyoxyethylene (12) sorbitan isostearate | 12.0 |
| polyoxyethylene (6) sorbitan coconut oil fatty acid ester | 2.0 |
| diethylene glycol ethyl ether | 20.0 |
| sorbitol solution (70%) | 15.0 |
| κ-carrageenan | 0.4 |
| xanthan gum | 0.2 |
| dibutylhydroxytoluene | 0.1 |
| perfume | 0.1 |
| purified water | the balance. |

While the invention has been described in detail and with reference to specific embodiments thereof, it will be apparent to one skilled in the art that various changes and modifications can be made therein without departing from the spirit and scope thereof.

What is claimed is:

1. An aqueous gel cleanser composition containing the following components (A), (B) and (C):

(A) from 1 to 50% by weight of a nonionic surfactant represented by the formula (1):

$$RCOO-(CH_2CH_2O)_n-H \quad (1)$$

wherein RCO represents a saturated or unsaturated acyl group having 4 to 30 carbon atoms; and n represents a number of from 1 to 50 on the weight average;

(B) from 20 to 70% by weight of a polyhydric alcohol or a glycol ether; and (C) from 0.1 to 5% by weight of a water soluble polymer.

2. An aqueous gel cleanser composition as claimed in claim 1, wherein said component (B) is selected from the group consisting of ethylene glycol, propylene glycol, isoprene glycol, dipropylene glycol, glycerol, 1,3-butylene glycol, sorbitol and diethylene glycol monoethyl ether.

3. An aqueous gel cleanser composition as claimed in claim 1 or 2, wherein said component (C) is selected from the group consisting of pectin, carrageenan, guar gum, locust bean gum, gelatin, xanthan gum, carboxyvinyl polymer, carboxymethylhydroxyethylcellulose, hydroxyethylcellulose, alginates, starch, polyvinyl alcohol, polyacrylates, polymethylacrylates and polyethylene glycol.

4. An aqueous gel cleanser composition as claimed in claim 1, wherein said component (B) comprises a polyhydric alcohol together with a glycol ether.

5. An aqueous gel cleanser composition as claimed in claim 1, wherein said component (C) comprises ι-carrageenan, κ-carrageenan and xanthan gum.

6. An aqueous gel cleanser composition as claimed in claim 1, which further contains a nonionic surfactant other than the one of the component (A).

7. An aqueous gel cleanser composition as claimed in claim 6, wherein said nonionic surfactant other than the one of the component (A) is selected from the group consisting of polyoxyethylene sorbitan fatty acid esters, ethylene oxide derivatives of glycerol fatty acid esters, ethylene oxide derivatives of propylene glycol fatty acid esters, polyoxyethylene alkyl ethers, polyoxypropylene alkyl ethers, polyoxyethylene alkylphenyl ethers and polyoxyethylene hardened castor oil.

* * * * *